US010470545B2

(12) United States Patent
Thiebaut et al.

(10) Patent No.: US 10,470,545 B2
(45) Date of Patent: Nov. 12, 2019

(54) SYSTEM INCLUDING A BRUSH, HAIR DRYER, AND CLIENT DEVICE TO ASSIST USERS TO ACHIEVE THE BEST DRYING AND STYLING PERFORMANCE

(71) Applicant: L'OREAL, Paris (FR)

(72) Inventors: Geraldine Thiebaut, Clichy (FR); Helga Malaprade, Clichy (FR); Gregoire Charraud, Clichy (FR); Guive Balooch, Clark, NJ (US)

(73) Assignee: L'OREAL, Paris (FR)

( * ) Notice: Subject to any disclaimer, the term of this patent is extended or adjusted under 35 U.S.C. 154(b) by 102 days.

(21) Appl. No.: 15/721,320

(22) Filed: Sep. 29, 2017

(65) Prior Publication Data

US 2019/0098978 A1    Apr. 4, 2019

(51) Int. Cl.
| | |
|---|---|
| *A45D 20/12* | (2006.01) |
| *A61B 5/00* | (2006.01) |
| *A45D 44/00* | (2006.01) |
| *A46B 15/00* | (2006.01) |
| *A46B 9/02* | (2006.01) |
| *A45D 24/00* | (2006.01) |
| *H04B 7/26* | (2006.01) |

(52) U.S. Cl.
CPC .......... *A45D 20/12* (2013.01); *A45D 44/005* (2013.01); *A46B 9/023* (2013.01); *A46B 15/0006* (2013.01); *A46B 15/0038* (2013.01); *A61B 5/448* (2013.01); *A45D 2024/002* (2013.01); *A46B 15/0004* (2013.01); *H04B 7/26* (2013.01)

(58) Field of Classification Search
CPC .... A45D 20/12; A45D 44/05; A45D 2024/02; A46B 15/004; A46B 15/0038; A46B 5/448; H04B 7/26

USPC ............................................................. 34/97
See application file for complete search history.

(56) References Cited

U.S. PATENT DOCUMENTS

| | | | | |
|---|---|---|---|---|
| 4,542,284 A | * | 9/1985 | Thaler .................. | G08B 21/185 219/492 |
| 5,636,318 A | * | 6/1997 | Polaert ................. | A45D 20/12 34/268 |

(Continued)

FOREIGN PATENT DOCUMENTS

| | | |
|---|---|---|
| WO | WO 2017/068429 A2 | 4/2017 |
| WO | WO 2017/068429 A3 | 4/2017 |

(Continued)

OTHER PUBLICATIONS

Lee et al, "Hair Shaft Damage from Heat and Drying Time of Hair Dryer," Ann Dermatol, vol. 23, No. 4, pp. 455-462, 2011.

(Continued)

*Primary Examiner* — Stephen M Gravini
(74) *Attorney, Agent, or Firm* — Oblon, McClelland, Maier & Neustadt, L.L.P.

(57) ABSTRACT

A system is provided that includes a hair dryer; a hairbrush; and a client device. The hairbrush is configured to sense a characteristic of at least one of the user's hair and the hair dryer, and to transmit information back to the hair dryer based on the sensed characteristic, and the client device is configured to communicate with the hair dryer and provide feedback to the user regarding a user's usage of at least one of the hair dryer and hairbrush based at least in part on sensed characteristic captured by the hairbrush.

16 Claims, 10 Drawing Sheets

(56) References Cited

U.S. PATENT DOCUMENTS

| | | | | |
|---|---|---|---|---|
| 5,857,262 | A * | 1/1999 | Bonnema | A45D 20/06 34/97 |
| 6,784,775 | B2 * | 8/2004 | Mandell | A45D 20/12 335/206 |
| 7,093,376 | B2 * | 8/2006 | Regen | A45D 20/12 132/200 |
| 7,356,943 | B2 | 4/2008 | Behbehani | |
| 7,913,416 | B1 * | 3/2011 | Scieri | A45D 20/10 34/96 |
| 7,946,056 | B2 * | 5/2011 | Kroll | A45D 20/22 132/233 |
| 8,707,969 | B2 * | 4/2014 | Seng | A45D 1/28 132/211 |
| 8,984,763 | B2 * | 3/2015 | Savarese | F26B 3/28 34/266 |
| 9,839,274 | B1 * | 12/2017 | Brickner | A45D 20/12 |
| 10,021,952 | B2 * | 7/2018 | Goldman | A45D 20/12 |
| 2003/0068057 | A1 * | 4/2003 | Miller | H04B 1/385 381/334 |
| 2003/0103767 | A1 | 6/2003 | Kakuya et al. | |
| 2004/0040948 | A1 * | 3/2004 | Mandell | A45D 20/12 219/222 |
| 2009/0099836 | A1 * | 4/2009 | Jacobsen | G06F 17/289 704/3 |
| 2014/0261518 | A1 * | 9/2014 | Savaides | A61K 8/65 132/206 |
| 2015/0342515 | A1 | 12/2015 | Hutchings et al. | |
| 2018/0184796 | A1 * | 7/2018 | Balooch | G09B 19/003 |

FOREIGN PATENT DOCUMENTS

| | | | | |
|---|---|---|---|---|
| WO | WO-2018023117 | A1 * | 2/2018 | A45D 20/12 |
| WO | WO-2018023119 | A1 * | 2/2018 | A45D 20/12 |

OTHER PUBLICATIONS

M. Gamez-Garcia, "The cracking of human hair cuticles by cyclical thermal stresses," J. Cosmet. Sci., 49, pp. 141-153, May/Jun. 1998.

R. McMullen, "Thermal degradation of hair. I. Effect of curling irons," J. Cosmet. Sci., 49 , pp. 223-244, Jul./Aug. 1998.

Rubenfeld et al, "Temperature Dependence of the Mechanical Properties of Human Hair in Relation to Structure," J. Soc. Cosmetic Chemists, 17, pp. 525-538, 1966.

International Search Report and Written Opinion dated Feb. 22, 2019 in PCT/US2018/053115, 14 pages.

* cited by examiner

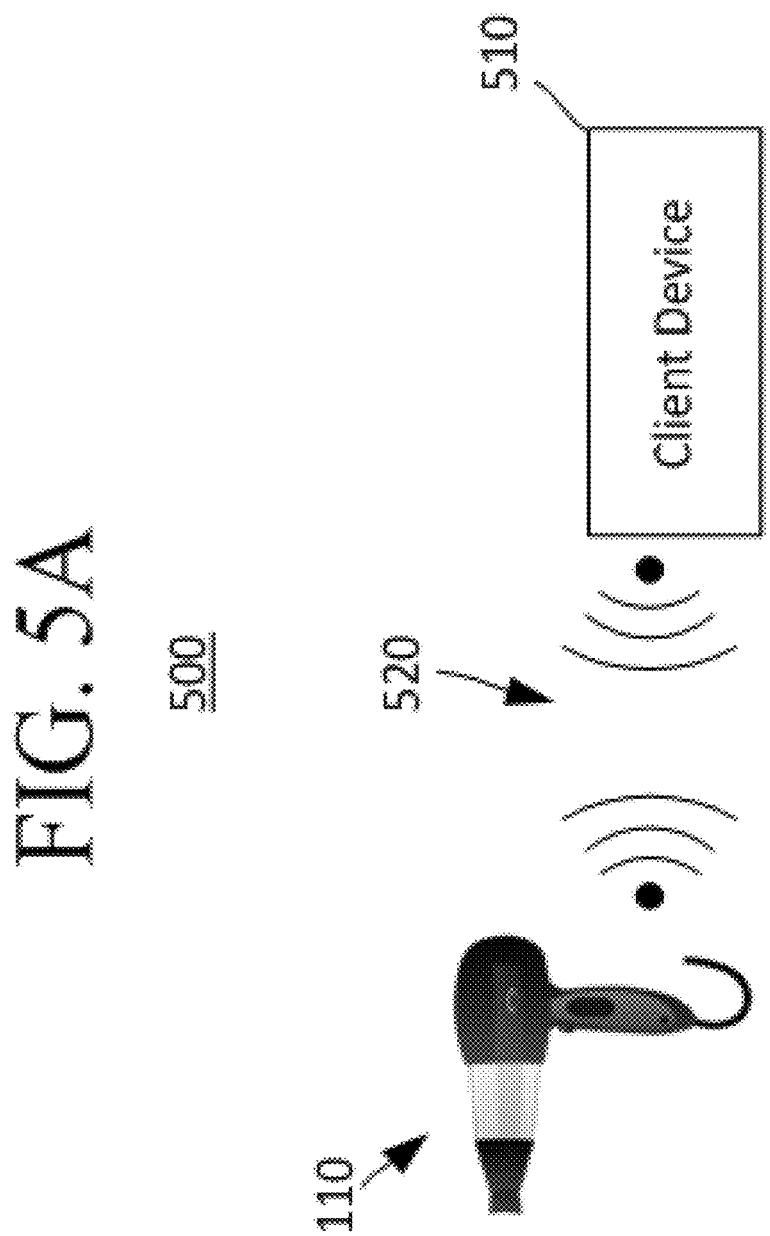

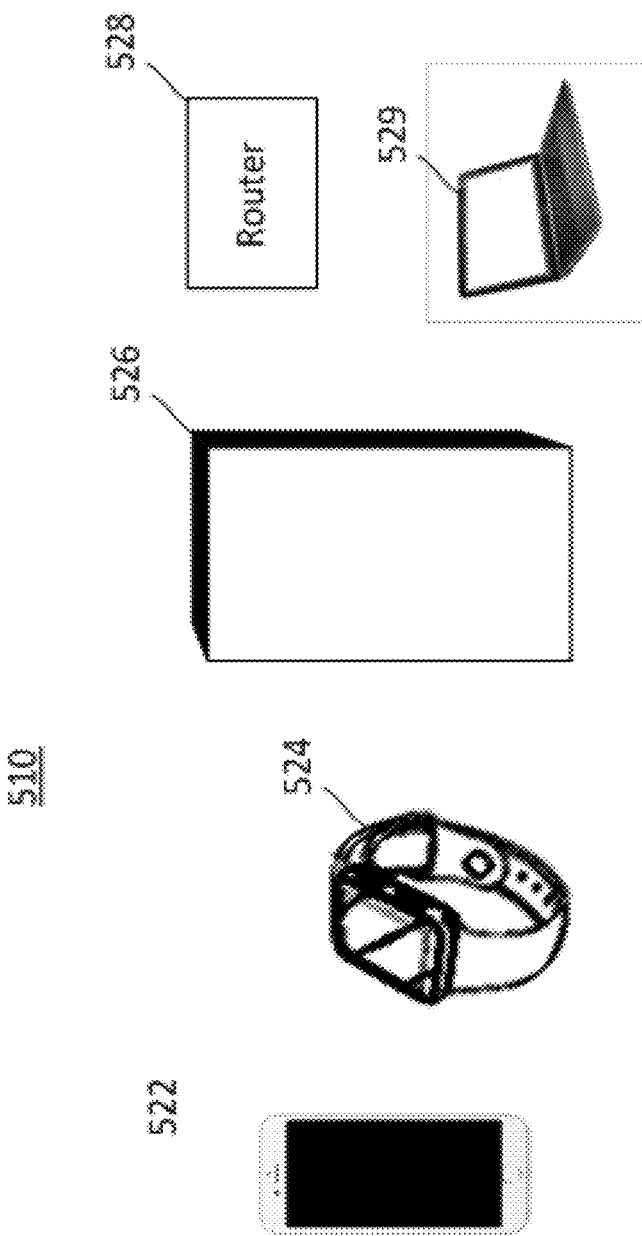

550

SYSTEM INCLUDING A BRUSH, HAIR DRYER, AND CLIENT DEVICE TO ASSIST USERS TO ACHIEVE THE BEST DRYING AND STYLING PERFORMANCE

BACKGROUND

Field

The present disclosure describes a system that provides a connection for feedback communication between a hair dryer and a grooming instrument (e.g., a hair grooming instrument, a brush, a hairbrush, a hair styling instrument, a styling brush, a comb, and the like).

SUMMARY

According to an embodiment, a system is provided comprising a hair dryer; a grooming instrument (e.g., a hair grooming instrument, a brush, a hairbrush, a hair styling instrument, a styling brush, a comb, and the like); and a client device, wherein the grooming instrument is configured to sense a characteristic of at least one of the user's hair and the hair dryer, and to transmit information back to the hair dryer based on the sensed characteristic, and the client device is configured to communicate with the hair dryer and provide feedback to the user regarding a user's usage of at least one of the hair dryer and grooming instrument based at least in part on sensed characteristic captured by the grooming instrument.

According to an embodiment, a system is provided comprising a hair dryer; a hairbrush; and a client device, wherein the hairbrush is configured to sense a characteristic of at least one of the user's hair and the hair dryer, and to transmit information back to the hair dryer based on the sensed characteristic, and the client device is configured to communicate with the hair dryer and provide feedback to the user regarding a user's usage of at least one of the hair dryer and hairbrush based at least in part on sensed characteristic captured by the hairbrush.

According to an embodiment, the client device is configured to output assessment information on the user's use of the at least one of the hair dryer and hairbrush to output guidance information on a method of using the styling tool to achieve a target hair health.

According to an embodiment, the guidance information is image data, video data, or audio data on using the styling tool to achieve the desired result.

According to an embodiment, the client device is configured to receive user information regarding physical characteristics of the user and outputs the guidance information based on the received user information.

According to an embodiment, the outputted assessment information and guidance information is based on measured data received for a single continuous session of the user using the styling tool.

According to an embodiment, the outputted assessment information is based on measured data received for a predetermined period of time that includes multiple sessions of the user using the styling tool.

According to an embodiment, the client device is configured to actuate a discovery protocol that causes the client device and the hair dryer to identify each other and to negotiate one or more pre-shared keys, and wherein the hair dryer and the client device are configured to exchange encrypted and anonymized information using the pre-shared keys.

According to an embodiment, the discovery protocol is configured to cause the client device and hair dryer to exchange treatment regimen information depending on at least one of the specific type of hair dryer, the specific type of hairbrush, and specific detected accessories of the hair dryer or hairbrush.

According to an embodiment, a method is provided implemented by a system that includes a hair dryer, a hairbrush, and a client device, comprising: sensing, by the hairbrush, a characteristic of at least one of the user's hair and the hair dryer, and to transmitting information back to the hair dryer based on the sensed characteristic, and communicating, by the client device, with the hair dryer and providing feedback to the user regarding a user's usage of at least one of the hair dryer and hairbrush based at least in part on sensed characteristic captured by the hairbrush.

BRIEF DESCRIPTION OF THE DRAWINGS

A more complete appreciation of the embodiments and many of the attendant advantages thereof will be readily obtained as the same becomes better understood by reference to the following detailed description when considered in connection with the accompanying drawings, wherein:

FIG. 5A shows a system that includes a client device and the hair dryer according to an embodiment.

FIG. 5B shows examples of a client device according to an embodiment.

DETAILED DESCRIPTION

Blow drying (use of a hair dryer with a brush to style hair while drying it) is commonly used and can cause hair damage such as roughness, dryness, brittleness, loss of hair color and eventually hair breakage. Studies have shown that hair damage increases with temperature (and temperature increases when distance between hair hair dryer and hair decreases or when concentrator nozzles are used) and drying duration.

The present applicants have recognized that by monitoring brushing pattern, and hair aggressions, and by connecting wirelessly instrumented brush/comb and blow-dryer, an automated and smart feedback loop can be setup between the two devices. The system can limit hair damage and provide feedback to the users and coach her/him to improve her/his brushing technique to achieve best drying/styling performance. It can also provide recommendations on a personalized or best fitted product to improve drying and styling performance and decrease/limit hair damage.

The present embodiments have the following objectives:
Monitor hair aggression, brushing patterns/movements,
Control temperature and air flow of the hair dryer Provide feedback (live or not) and coaches the user on her/his brushing/drying technique Improve brushing technique—empower users to achieve best daring/styling performance/result Prevent/limit hair damage Provide recommendations on personalized or adapted products and hair styles Provide refined ergonomy to reach highest compliance rate and increase monitoring and coaching performance.

Figure 1:
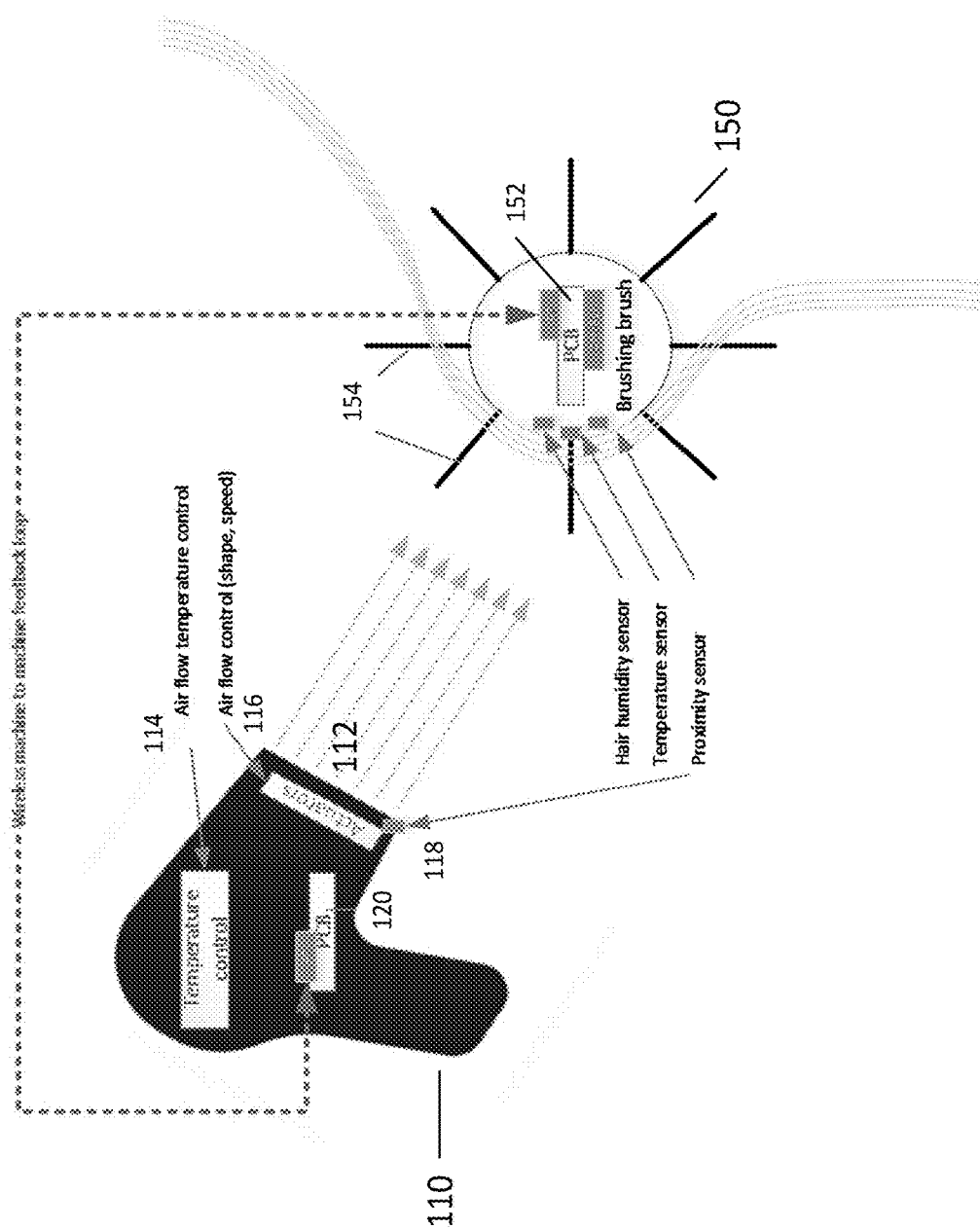
FIG. 1 shows a system that includes a hairbrush and a hair dryer according to an embodiment.

FIG. 1 shows a system 100 according to an embodiment. The system 100 includes a hair dryer device 110 and a brush device 150. The hair dryer 110 performs the functionality of a conventional hair dryer, such as generating and emitting hot air from outlet 112. The brush 150 includes bristles 154, which are disposed around the axis of the brush (a "round" hairbrush type). However, additional known hairbrush types may be used as well.

Additionally, the hair dryer device 110 and the brush device 150 include additional components. For instance, the hair dryer device 110 further includes a temperature controller 114 and actuators 116. The temperature controller 114 controls and adjusts the temperature of the air emitted by the hair dryer. The actuators control a shape of a pattern of air flow and the speed of air flow. The actuators may be mobile mechanical parts that could be moved in the air flow to modify its shape. Such air flow control is understood in the art, as evidenced by EP1779745 A1, which is incorporated herein by reference.

The hair dryer may further include a proximity sensor 118 preferably disposed near the outlet 112 of the hair dryer. The proximity sensor may be an optical sensor, such as an infrared sensor, which is understood in the art. However other examples may be employed as well, such as a capacitive, ultrasonic, or Doppler sensors.

In an embodiment, the hair dryer device 110 is configured to vary at least one setting at the hair dryer based on the received sensed characteristic. In an embodiment, the hair dryer device 110 is configured to dynamically modulate at least one setting at the hair dryer based on the received sensed characteristic.

The hair dryer may further include a printed circuit board (PCB) 120 that includes communication and control circuitry such as a wireless RF communication interface for performing wireless communication with an external device (such as the brush device 150).

The brush device may further include its own PCB 180 that includes communication and control circuitry such as a wireless RF communication interface for performing wireless communication with an external device (such as hair dryer 150). The PCB may further hold a motion detector, such as an accelerator/gyrometer.

The brush device also may include a hair humidity sensor and a temperature sensor. Hair and humidity sensors are known and understood in the art.

As depicted in FIG. 1, there may be a wireless machine-to-machine feedback loop between the brush device 150 and the hair dryer 110, facilitated by communication between the wireless RF communication interface embedded in each device. In such a feedback loop, the brush can sense the temperature when the hair dryer is operational and the humidity level of the user's hair and provide such feedback to the hair dryer. Based on this information, the hair dryer may adjust the temperature and/or the shape and/or speed of the air flow, by for example, adjusting the resistance of the heating element in the hair dryer, adjusting the fan speed, and/or adjusting the shape of the mechanical elements which control the air flow shape.

Figure 2:
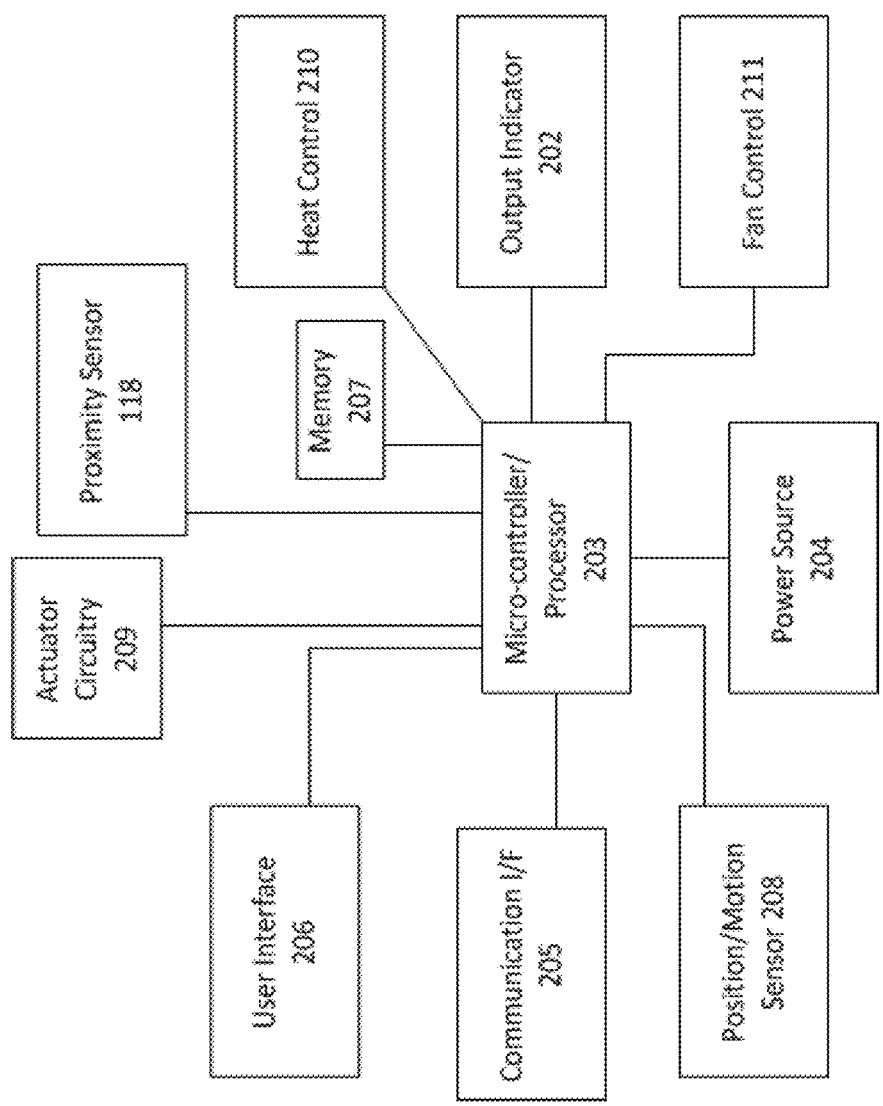
FIG. 2 shows a hardware configuration of a hair dryer according to an embodiment.

FIG. 2 shows a diagram of the electrical block diagram of the hardware components of the hair dryer according to an embodiment. The power from the power source 204 is controlled by the micro-controller/processor 203. It will be appreciated that the electrical block diagram may be modified to adapt to other configurations in accordance with the principles disclosed herein.

In an example, the communication interface (I/F) 205 can include circuitry and hardware for communication with a client device 120. The communication interface 205 may include a network controller such as BCM43342 Wi-Fi, Frequency Modulation, and Bluetooth combo chip from Broadcom, for interfacing with a network. The hardware can be designed for reduced size. For example, the processor 203 may be a CPU as understood in the art. For example, the processor may be an APL0778 from Apple Inc., or may be other processor types that would be recognized by one of ordinary skill in the art. Alternatively, the CPU may be implemented on an FPGA, ASIC, PLD or using discrete logic circuits, as one of ordinary skill in the art would recognize. Further, the CPU may be implemented as multiple processors cooperatively working in parallel to perform the instructions of the inventive processes described above.

In an embodiment, the hair dryer includes a user interface 206, which may be in the form of input buttons on the housing of the tool, or it may be in the form of a contact-sensitive display, such as a capacitive or resistive touch screen display.

In an embodiment, the hair dryer includes output indicator 202 which may be in the form of lights (such as LED lights), an indicator on a touch screen, or an audible output through a speaker.

In an embodiment, the hair dryer includes a memory 207 that stores software for controlling the hair dryer, or for storing user data or other information.

In an embodiment, the hair dryer includes a position/motion sensor 208 that can detect an orientation of the hair dryer too as it is being held by the user, and it may also detect movements and motion paths of the hair dryer as well. In an embodiment, the position/motion sensor is at least one of or a combination of a geomagnetic sensor and an acceleration sensor. For example, a 3-axis geomagnetic sensor ascertains the direction of geomagnetism, or in other words a geomagnetic vector Vt, given the current orientation of (the housing of) the styling tool housing the 3-axis geomagnetic sensor. A 3-axis acceleration sensor ascertains the direction of gravity, or in other words a gravity vector G, given the current orientation of (the housing of) the styling tool housing the 3-axis acceleration sensor in a still state. The gravity vector G matches the downward vertical direction. The gravity vector G likewise may be decomposed into Xs, Ys, and Zs axis components.

Alternatively, or additionally, a gyroscope may be used which is a sensor that detects angular velocity about the three axes Xs, Zs, and Ys (roll, pitch, and yaw), and is able to detect the rotation of an object. In addition, the geomagnetic sensor is able to ascertain the heading in which the object faces, based on a geomagnetic vector as discussed earlier.

The hair dryer may include actuator circuitry 209 that is used to control the shape of the mechanical elements which control the airflow shape.

The hair dryer includes proximity sensor 118, which is discussed above.

The hair dryer includes heat control circuitry 210, which is used to control the heat by varying the resistance of the heating element in the hair dryer as discussed above.

The hair dryer further includes fan control 211 which is use to vary the speed of the blower fan in the in the hair dryer as discussed above.

Figure 3:
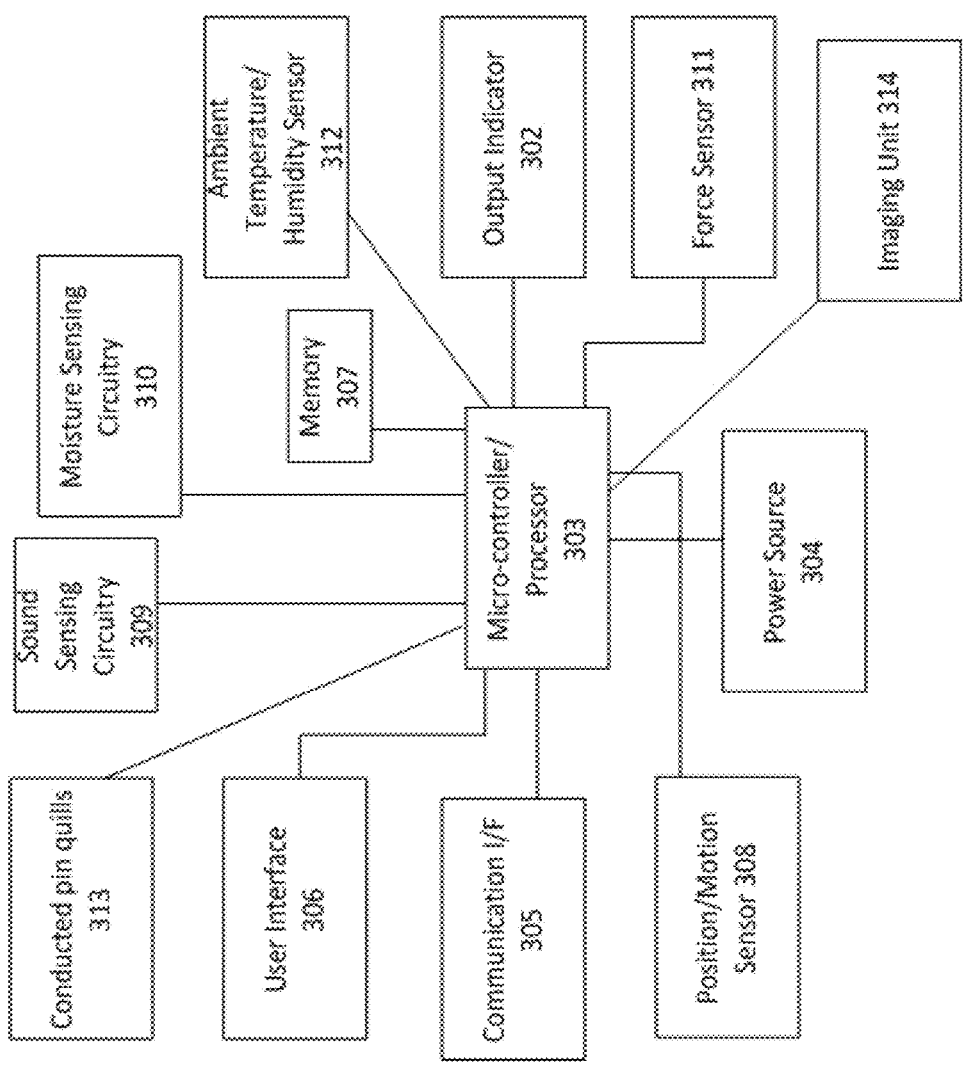
FIG. 3 shows a hardware configuration of a hairbrush according to an embodiment.

FIG. 3 shows a diagram of the electrical block diagram of the hardware components of the hairbrush according to an embodiment. Similar to the hair dryer above, the hairbrush includes a micro-controller/processor 303, a power source 304, a communication interface 305, a user interface 306, a memory 307, and a position/motion sensor 308.

The hairbrush may also include sound sensing circuitry 309, which may include a microphone to detect the dryness of the user's hair based on day-to-day energy and spectral sound variation.

The hairbrush may also include moisture sensing circuitry 311. This circuitry may be similar to that described in U.S. application Ser. No. 13/112,533 (US Pub. No. 2012/0291797A1), incorporated herein by reference. Alternatively, the moisture sensing circuitry may rely on a hall-effect sensor which detects changes in a magnetic field, such changes being sensitive to a moisture level.

The hairbrush may also include a force sensor 311, which may be in the form of a load cell disposed between the head and handle.

The hairbrush may also include an ambient temperature/humidity sensor 312, discussed above, that detects the local temperature or humidity near the hairbrush.

Additionally, the hairbrush may include conducted pin quills 313 embedded in the hairbrush for detecting if the hair is wet or dry, or for detecting contact with the hair of the user.

The hairbrush may also include an imaging unit 314, which may be a camera disposed on an outer surface of the brush which faces the users' head or hair while the user is using the hairbrush. The imaging unit may optionally have a thermal imaging capability for sensing thermal characteristics of the user's hair. The imaging unit may also be equipped with a lighting unit (such as an LED light) to aid in the imaging process.

As noted above, the brush and hair dryer are equipped with means to communicate with one another and the hair dryer is equipped with a control system calibrated to adapt the temperature and the air flow depending on the indicators of hair damage/aggression and/or on a styling result selected by the user. Therefore, intelligence and algorithms embedded in the brush and/or the hair dryer or deported, can translate the sensor records into adjustments at the hair dryer.

Figure 4A:
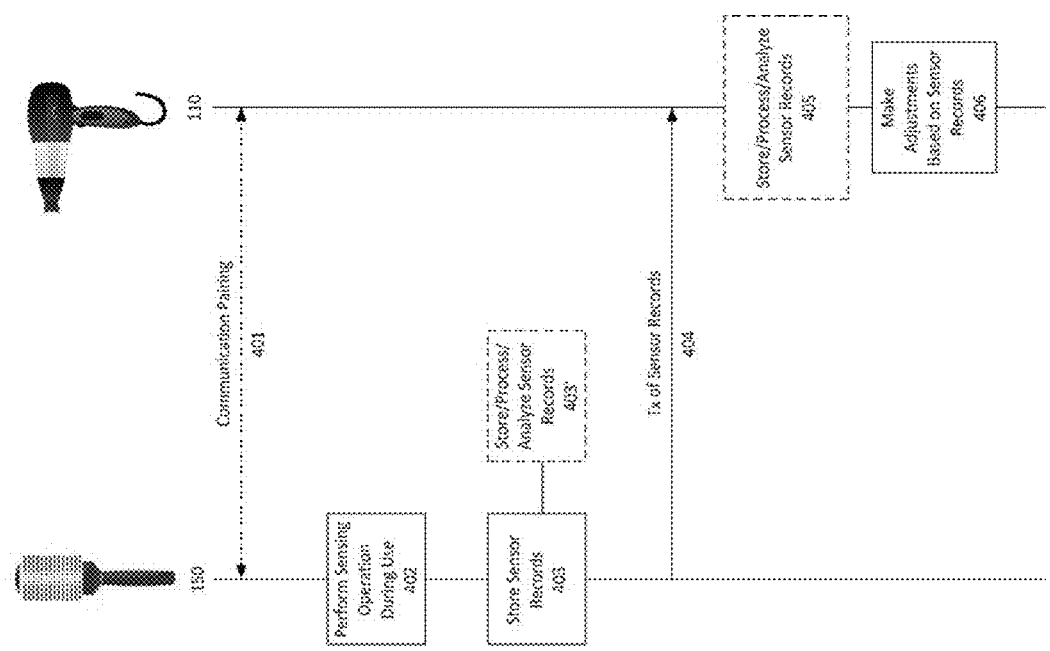
FIGS. 4A, 4B, and 4C show process that occur between and at each of the hair dryer and the hairbrush according to an embodiment.

FIG. 4A shows general processes performed among the hair dryer and the hairbrush. As one process show in FIG. 4A, communication pairing 401 is performed between the two devices when the two devices are within an acceptable wireless communication range of each other. Such pairing will depend on the type of communication protocol being used and such protocols are well understood in the art. The user may use the hairbrush, and during such use, the hairbrush will perform any of a number of sensing operations as was described above (step 402). The sensing operations do not need to occur while the hair dryer is simultaneously being used, and they can be started and completed at any time based on receiving a user input to start/finish such sensing. The sensor records obtained by the sensing operations may be stored in a memory (step 403) and/or immediately communicated to the hair dryer (step 404).

As shown in FIG. 4A, the hair dryer stores the sensor records received from the hair dryer, and the performs processing and analyzing of the sensor records (step 405). Then, the hair dryer makes adjustments to the hair dryer based on the processing and analysis of the sensor records (step 406).

In FIG. 4A, the communication pairing does not need to occur prior to the user using the hairbrush to perform the sensing operation at 402, and it can occur any time before the hairbrush transmits the sensor records to the hairbrush.

Additionally, the hairbrush does not necessarily need to perform the processing and analyzing of the sensor records as shown in step 405. In this situation, the hair dryer may transmit the sensor records to an external client device (such as a smartphone or user computer) for controlling performance of the processing and analyzing of the sensor records as will be discussed in further detail below. Additionally, as shown in optional step 403', the hairbrush may perform at least some processing and/or analysis on the sensor records prior to transmitting information to the hairbrush.

Figure 4B:
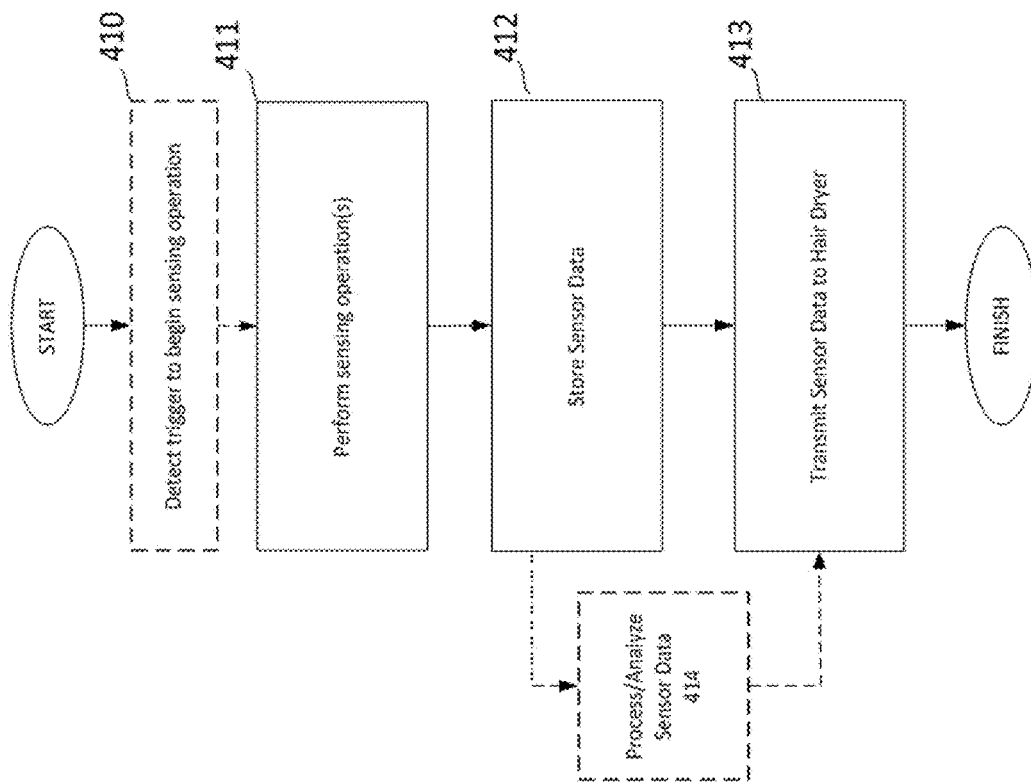

FIG. 4B shows an algorithm that may be performed by the hairbrush according to an embodiment. In step 410, the hairbrush detects a trigger to begin sensing operation. This trigger may be a deliberate user input at the user interface of the hairbrush to start one or more sensing operations. The trigger may also be received from the hair dryer itself. For instance, if communication pairing has been established between the hair dryer and the hairbrush, the hair dryer may transmit a signal to the hairbrush to begin the sensing operation. Such transmission of the signal may be tied to the user activating the blowing operation of the hair dryer, or it may be based on a proximity sensor of the hair dryer detecting that the hair dryer is within a range of the user's head or the hairbrush.

In step 411, the sensing operation(s) is/are performed at step 411. The types of sensing operations performed by the hairbrush are described in detail above. In step 412, the sensor data obtained from the sensing operations are stored in the memory of the hairbrush as they are obtained. In step 413, the sensor data is transmitted to the hair dryer. Optionally, in step 414, the hairbrush may perform at least some processing and/or analysis of the sensor data prior to transmitting the sensor data to the hair dryer. The results of such processing and/or analysis would then also be transmitted to the hair dryer in step 413 along with (or even without the sensor data). Such transmission may be made when the data is accumulated after a total amount of time, it may occur periodically, it may occur based on user input at the user interface of the hairbrush, or it may occur based on a request signal received from the hair dryer.

Figure 4C:
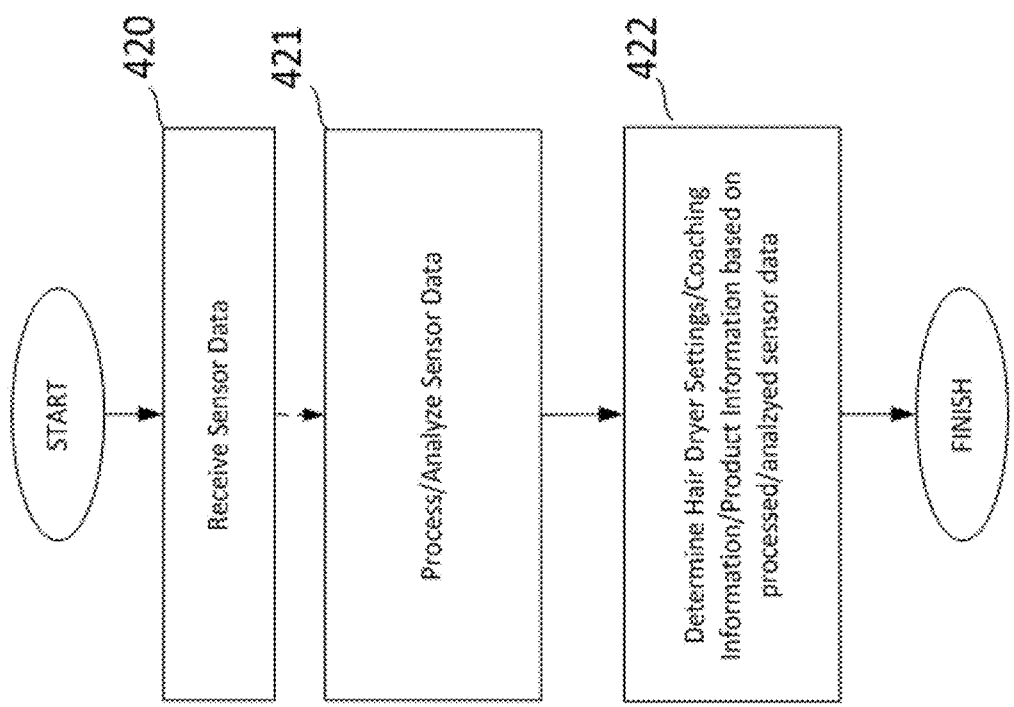

FIG. 4C shows an algorithm that may be performed by the hair dryer according to an embodiment. In step 420, the hair dryer receives the sensor data, which as discussed above, may be made when the data is accumulated at the hairbrush after a total amount of time, it may occur periodically, it may occur based on user input at the user interface of the hairbrush, or it may occur based on a request signal received from the hair dryer which may be triggered by a user input at the hair dryer or it could be based on an event such as the user turning off the blowing operation (while not powering off the hair dryer). In step 421, the sensor data is processed or analyzed, which will be explained in more detail below. In step 422, the hair dryer performs adjustment of the settings on the hair dryer based on the processed/analyzed sensor data, which will be discussed in more detail below.

As discussed above, in step 421, the sensor data is processed or analyzed by the hair dryer (or another device as will be discussed below). The specific type of analysis will depend on the type of sensing that occurred and the goal of the analysis.

For instance, brushing patterns and movements of the user when using the hairbrush either alone or in combination with the hair dryer may be determined based on a combination of data obtained from the force/effort sensors, accelerometer and gyroscope, magnetic compass, contact sensor, and proximity sensor. The following brushing patterns and movements may be determined from this data.

Pulling force of the user
Hair twisting and wrapping of hair around the brush
Localized brushing movements
Proximity of hairbrush with hair dryer The sensor data can also be used to assess hair characteristics/damage/aggression or risk levels for damaging hair based on a combination of data obtained from the sensed ambient temperature and humidity, the temperature and humidity of hair in contact with the brush, the conductance sensor, thermal camera, microphone, contact sensor, proximity sensor, and force/effort sensor. The following hair characteristics/damage/aggression or risk levels may be determined from this data.

Hair temperature and humidity
A cumulative thermal aggression level (temperature or hair damage risk level×duration)
Increased hair damage risk level related to hair humidity
Hair shininess level estimated from image analysis of images acquired with the camera
Color fading level estimated from image analysis of images acquired with the camera
Hair roughness level The present embodiments are directed to a smart, hair dryer device and system that teaches a user how to achieve any style at home. In an embodiment, the system connects the hair dryer with a client device. In an embodiment, the client device receives inputs on the user's needs provides feedback on how to achieve a certain look, and can correct the user's technique while using the styling tool.

FIG. 5A shows a system 500 that includes the hair dryer 110 and a client device 510. In an embodiment, the hair dryer 110 is in communication with the client device 501 with a wireless signal 520. In an embodiment, the client device 510 is configured to operate a software application or set of software modules to receive and send communications from and to the hair dryer 110. In an example, the software application can send a protocol or target profile to the hair dryer 110, as well as receive data from the hair dryer 110 to track the usage in real time.

FIG. 5B shows different examples of the client devices 120 including, a mobile device 522, a wearable electronic 524, a television or magic mirror 526, a network router 528, and a personal computer 529.

The wireless signal 520 can be any appropriate signal such as an electromagnetic signal including WIFI, Bluetooth, near-field, or any other signal such as optical, and acoustic. Each client device, including the appliance, may communicate with each other through an internet connection via an 802.11 wireless connection to a wireless internet access point, or a physical connection to the internet access point, such as through an Ethernet interface. Each connected device is capable of performing wireless communication with other devices, such as through a Bluetooth connection or other wireless means as well.

Figure 5C:
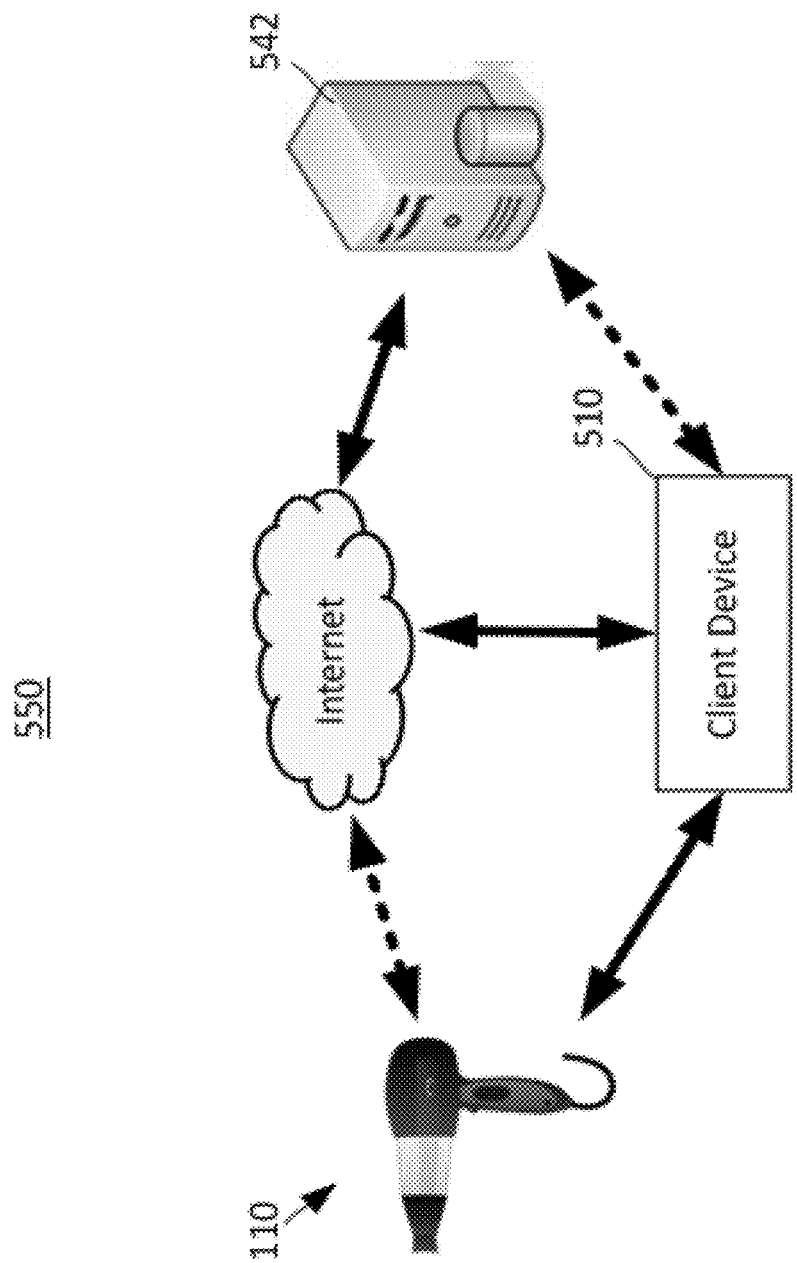
FIG. 5C. shows a system to promote optimum performance of a hair dryer that includes a client device and at least one external server according to an embodiment.

FIG. 5C is a diagram representing an example of a system 550 to promote optimum performance of a hair dryer 110, according to one example. The system 550 includes at least the hair dryer and the client device. Optionally, the system 550 may further include one or more external servers 542 which are implemented as part of a cloud-computing environment and in communication with the system 550 through the Internet. The one or more external servers 542 can store user data, products such as hair products, hair dryer or brush accessories, protocols and routines, tutorials, as well as other $3^{rd}$ party services according to an example.

The user interface or the client device can display tutorials on how to use the hair dryer. The user interface can create and download protocols for a regimen or routine. The user interface can coach, track usage and compare the tracked usage to the protocol, the regimen, and the routine. The user interface can calculate a score based on the tracked usage. The user interface can store the scores and the tracked usage of the hair dryer in memory of the client device. The user interface can be used to make a purchase of any products related to the hair dryer. For instance, the hair dryer may be used with a combination of styling products or chemical compositions used for treating the user's hair, and the client device can output recommendations on particular styling products or compositions to be used, and which step in the process they are to be used, based on the desired results inputted by the user.

As an initial step, the client device collects information regarding a user's desired results. In an example, the user may use the client device to browse a database of images which depict various hair styles. In another example, the user may enter a keyword search to the client device to find a desired look. The client device may store search results locally or may connect to an external system or server to access the database or search results.

After the user finds a desired look to be achieved using the hair dryer, the user may access tutorials for using the hair dryer to achieve a target look. The tutorials may be in text form, still image form, video form, or audio-only form.

In addition to using the tutorials, the user may connect the client device 510 with the hair dryer over the wireless connection (such as the Bluetooth or Wi-Fi connection) to receive real-time feedback while using the hair dryer, or to record the usage of the hair dryer for later reporting or feedback.

For example, the hair dryer can communicate what settings are currently being used at the hair dryer.

For example, while using the hair dryer, the motion sensor on the hair dryer can output a detection motion of the hair dryer as feedback to the client device. The client device is configured to compare the detected motion with predetermined motion data for providing real-time performance results to the user to or to output instructions for the user to make a correction.

In another example, the temperature sensed by the hairbrush and communicated to the hair dryer can be communicated to the client device. The client device is configured to compare the detected temperature with predetermined temperature information for providing a warning to the user when the detected temperature is above a predetermined threshold.

In an example, a timer on the hairbrush may provide measured time information to the client device. The client device is configured to compare the measured time to a target time for providing an output to the user on the amount of time remaining for a certain action using the hair dryer, or to provide a warning to the user when a time target has elapsed. The target time may depend on the routine, the style to be achieved, and the current step in the process such that there may be different durations for the different steps. The client device is configured to receive input from the user to create a customer profile based on the personal characteristics of the user. For instance, the client device is configured to provide questions to the user such as "hair dyed or not?", "hair thick or thin?", and "hair straight or curly?". The customer profile can be used to select a specific tutorial or set of data to be used when measuring the performance from the hair dryer and brush. The client device may recommend or avoid recommending or proposing certain hair styles depending on the assessed type of hair, level of damage, or other parameters.

The client device can also have a camera function that can be used to provide inputs to the customer profile. For instance, the camera can take images of the user's hair to determine if a desired look is possible, or to make further recommendations to the user based on the characteristics or color of the hair or skin.

Alternatively, the client device can interface with known spectography tools to analyze the user's hair. Alternatively, the client device can interface with known chemical measuring tools to determine the chemical and structural properties of the user's hair. In an embodiment, the client device is configured to maximize personalization and safety for the user. The client device may warn a user if a setting is not recommended for the type of hair of the user. The client device may inquire if the user's hair is color-treated (including bleached), highlighted, keratin-treated or relaxed.

The client device may receive as an input the level of moisture or porosity or the hair (which may be assess by the stylist, or by the moisture sensor on the styling tool).

The client device may provide a warning if the hair is not ready to receive additional heat, such as if the moisture sensor in the hairbrush detects too much dryness.

The client device may provide instructions to pre-treat the user's hair before applying heat. The client device may advise if the initial temperature is right for the style the user is trying to achieve since different levels of temperatures are suitable for different hair quality levels.

The client device can have an automated setup or control, such as providing automated temperature control from the client device from the phone.

The client device is configured to upload data regarding the user to an external system or server (such as a cloud-based system). Such data may include the user profile, amount of use of the styling tool, or performance results when using the styling tool. The client device can also provide an option to keep the user data anonymous.

Furthermore, the circuitry of the client device may be configured to actuate a discovery protocol that allows the client device and the hair dryer to identify each other and to negotiate one or more pre-shared keys, which further allows the hair dryer and the client device to exchanged encrypted and anonymized information. The discovery protocol may further allow the client device and hair dryer to exchange treatment regimen information depending on the specific type of hair dryer, or hairbrush, or based on specific detected accessories.

The client device can use the camera function to provide a sharing feature, in which the user can upload photos taken before and/or after the use of the styling tool. The uploaded photos can be used for receiving feedback from professional hair stylists or other users. In an embodiment, the uploaded photos may be uploaded directly to a social media platform.

Figure 6:
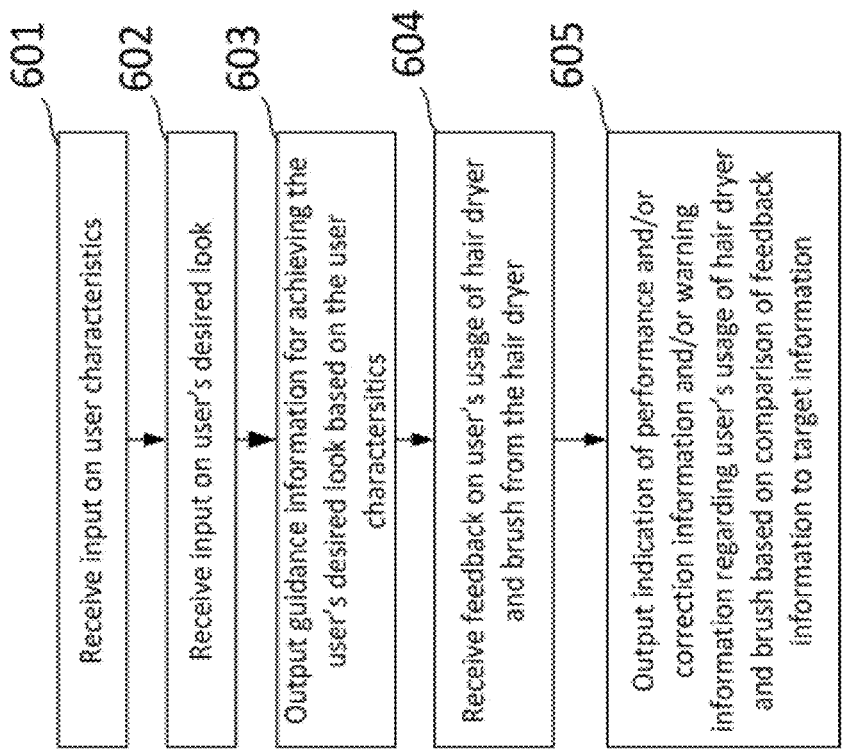
FIG. 6 shows a process performed by a client device according to an embodiment.

FIG. 6 shows a flowchart of a method performed by the client device based on the above-described features. In step 601, the client device receives an input from the user regarding the user's physical characteristics. In step 602, the client device receives an input from the user regarding a selection of a desired look to be achieved using the hair dryer and brush. In step 603, the client device outputs guidance information for achieving the user's desired look using the hair dryer and brush based on the user's selection and the user's physical characteristics. In step 604, after the user starts using the hair dryer and/or brush, the client device receives feedback on the user's usage of the styling tool from the styling tool (such as feedback from the various sensors incorporated into the hair dryer and brush and described above). In step 605, the client device outputs an indication of the user's performance based on a comparison of the feedback information received from the hair dryer and target information. Alternatively, the client device may output correction information (such as an adjustment of a movement of the hair dryer and/or brush or heat/air flow/ speed setting) based on the feedback information. Alternatively, the client device may output warning information (such as a warning related to a sensed temperature, moisture, or time elapsed) to the user based on the feedback information.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

What is claimed is:

1. A system, comprising:
a hair dryer;
a hairbrush; and
a client device,
wherein the hairbrush is configured to sense a characteristic of at least one of a user's hair and the hair dryer, and to transmit information back to the hair dryer based on the sensed characteristic, and
the client device is configured to communicate with the hair dryer and provide feedback to the user regarding the user's usage of at least one of the hair dryer and hairbrush based at least in part on sensed characteristic captured by the hairbrush.

2. The system according to claim 1, wherein the client device is configured to output assessment information on the user's use of the at least one of the hair dryer and hairbrush to output guidance information on a method of using the at least one of the hair dryer and hairbrush to achieve a target hair health.

3. The system according to claim 2, wherein the guidance information is image data, video data, or audio data on using the at least one of the hair dryer and hairbrush to achieve the desired result.

4. The system according to claim 2, wherein the client device is configured to receive user information regarding physical characteristics of the user and outputs the guidance information based on the received user information.

5. The system according to claim 2, wherein the outputted assessment information and guidance information is based on measured data received for a single continuous session of the user using the at least one of the hair dryer and hairbrush.

6. The system according to claim 2, wherein the outputted assessment information is based on measured data received for a predetermined period of time that includes multiple sessions of the user using the at least one of the hair dryer and hairbrush.

7. The system according to claim 1, wherein the client device is configured to actuate a discovery protocol that causes the client device and the hair dryer to identify each other and to negotiate one or more pre-shared keys, and wherein the hair dryer and the client device are configured to exchange encrypted and anonymized information using the pre-shared keys.

8. The system according to claim 7, wherein the discovery protocol is configured to cause the client device and hair dryer to exchange treatment regimen information depending on at least one of the specific type of hair dryer, the specific type of hairbrush, and specific detected accessories of the hair dryer or hairbrush.

9. A method implemented by a system that includes a hair dryer, a hairbrush, and a client device, comprising:
sensing, by the hairbrush, a characteristic of at least one of a user's hair and the hair dryer, and to transmitting information back to the hair dryer based on the sensed characteristic, and
communicating, by the client device, with the hair dryer and providing feedback to the user regarding the user's usage of at least one of the hair dryer and hairbrush based at least in part on sensed characteristic captured by the hairbrush.

10. The method according to claim 9, further comprising outputting, by the client device, assessment information on the user's use of the at least one of the hair dryer and hairbrush to output guidance information on a method of using the at least one of the hair dryer and hairbrush to achieve a target hair health.

11. The method according to claim 10, wherein the guidance information is image data, video data, or audio data on using the at least one of the hair dryer and hairbrush to achieve the desired result.

12. The method according to claim 10, wherein the client device is configured further comprising receiving, by the client device, of user information of the user and outputting the guidance information based on the received user information.

13. The method according to claim 10, wherein the outputted assessment information and guidance information is based on measured data received for a single continuous session of the user using the at least one of the hair dryer and hairbrush.

14. The method according to claim 10, wherein the outputted assessment information is based on measured data received for a predetermined period of time that includes multiple sessions of the user using the at least one of the hair dryer and hairbrush.

15. The method according to claim 9, further comprising actuating, by the client device, a discovery protocol that causes the client device and the hair dryer to identify each other and to negotiate one or more pre-shared keys, and wherein the hair dryer and the client device exchange encrypted and anonymized information using the pre-shared keys.

16. The method according to claim 15, wherein the discovery protocol causes the client device and hair dryer to exchange treatment regimen information depending on at least one of the specific type of hair dryer, the specific type of hairbrush, and specific detected accessories of the hair dryer or hairbrush.

\* \* \* \* \*